United States Patent
Stone et al.

(10) Patent No.: US 7,766,964 B2
(45) Date of Patent: Aug. 3, 2010

(54) IN SITU GRAFT PREPARATION FOR KNEE LIGAMENT RECONSTRUCTION

(75) Inventors: Kevin T Stone, Winona Lake, IN (US); Nathan M Sautter, North Manchester, IN (US); Michael D Lee, Fort Wayne, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 387 days.

(21) Appl. No.: 11/731,896

(22) Filed: Mar. 30, 2007

(65) Prior Publication Data
US 2008/0243248 A1 Oct. 2, 2008

(51) Int. Cl.
*A61F 2/08* (2006.01)
(52) U.S. Cl. .............. 623/13.13; 623/13.11; 623/13.12; 623/13.14
(58) Field of Classification Search .............. 623/13.11, 623/13.12, 13.13
See application file for complete search history.

(56) References Cited

U.S. PATENT DOCUMENTS

| | | | | |
|---|---|---|---|---|
| 3,960,995 | A | * | 6/1976 | Kourkene .................... 264/431 |
| 5,004,474 | A | * | 4/1991 | Fronk et al. .............. 623/13.14 |
| 5,131,850 | A | * | 7/1992 | Brockbank ................. 435/1.3 |
| 5,171,273 | A | * | 12/1992 | Silver et al. .............. 623/13.11 |
| 5,172,683 | A | | 12/1992 | West |
| 5,298,012 | A | | 3/1994 | Handlos |
| 5,351,675 | A | | 10/1994 | Brodsky |
| 5,931,869 | A | | 8/1999 | Boucher et al. |
| 6,231,596 | B1 | | 5/2001 | Collins |
| 6,254,605 | B1 | | 7/2001 | Howell |
| 6,280,472 | B1 | | 8/2001 | Boucher et al. |
| 6,482,232 | B1 | | 11/2002 | Boucher et al. |
| 6,679,889 | B1 | * | 1/2004 | West et al. .................... 606/88 |
| 6,755,840 | B2 | | 6/2004 | Boucher et al. |
| 6,796,977 | B2 | | 9/2004 | Yap et al. |
| 7,241,131 | B1 | * | 7/2007 | Booth et al. ................. 425/549 |
| 2003/0163087 | A1 | | 8/2003 | Noice et al. |
| 2004/0153153 | A1 | * | 8/2004 | Elson et al. ............... 623/13.14 |
| 2005/0119744 | A1 | * | 6/2005 | Buskirk et al. ........... 623/13.17 |
| 2005/0229323 | A1 | * | 10/2005 | Mills et al. .................... 8/94.11 |
| 2005/0234301 | A1 | | 10/2005 | Gomez |

OTHER PUBLICATIONS

William J. Ciccone II, M.D. et al, "Viscoelasticity and Temperature Variations Decrease Tension and Stiffness of Hamstring Tendon Grafts Following Anterior Cruciate Ligament Reconstruction", JBJS The Journal of Bone & Joint Surgery, downloaded from www.ejbjs.org on May 4, 2006, (pp. 1071-1078).

* cited by examiner

*Primary Examiner*—Thomas J Sweet
*Assistant Examiner*—Timothy J Gosart
(74) *Attorney, Agent, or Firm*—Harness, Dickey

(57) ABSTRACT

Methods of ligament repair are provided. A ligament graft is arranged in a tensioning device and placed adjacent to a heating surface. The heating surface is activated to heat the graft. The graft is tensioned while on the substantially dry heating surface to provide laxity to the graft. The size of the relaxed graft remains the same until the graft is implanted in a bone tunnel as either an anterior or posterior cruciate ligament graft.

26 Claims, 4 Drawing Sheets

IN SITU GRAFT PREPARATION FOR KNEE LIGAMENT RECONSTRUCTION

FIELD

The present disclosure relates to methods and apparatuses for in situ graft preparation.

BACKGROUND

The knee joint is frequently the object of injury and is often repaired using arthroscopic surgical procedures. Common repairs to the knee joint include repair and reconstruction of damaged anterior cruciate ligaments (ACL) and posterior cruciate ligaments (PCL). When the ACL or the PCL have ruptured and are non-repairable, they may be independently replaced as needed and the knee reconstructed through the use of ligament grafts. The PCL may alternatively or additionally be replaced. The ACL and the PCL are three-dimensional structures with broad attachments and a continuum of fibers. These fibers are of different lengths, have different attachment sites, and are under different tensions.

To provide proper repair of the cruciate ligament defect, the ligament graft must be implanted into the defect site with the proper laxity. If there is too much relaxation in the ligament graft, hyperextension of the knee joint may result. If there is insufficient laxity in the ligament graft, the graft will be tight and the patient may not achieve the desired range of motion in the knee.

Current techniques of providing the ligament graft to the defect site include stretching the ligament graft while the graft is being soaked in a saline solution. Shortcomings of this technique are that the saline solution can cause unpredictability in the final size of the graft due to shrinkage of the graft and that the saline bath and the stretching of the graft may happen too remotely from the surgical table thereby causing the graft to become misshapen prior to implantation. Other techniques include stretching the graft and then storing the graft in a trough of a warm solution until the surgeon is ready to implant the graft.

These and other current techniques facilitate changes in graft size during graft preparation and implantation. In some instances, between tensioning the graft and transferring the graft to a warming source, the graft can change size multiple times. This is not desirable because upon implanting the graft, there may be additional relaxation of the graft due to in vivo conditions. If the graft is not prepared and maintained in a manner where the predictability of the graft size in vivo is known or can be controlled, the graft will additionally relax after implantation thereby causing hyperextension of the knee.

Accordingly, there is a need for improved methods for preparing ligament grafts. There is also a need for surgical methods which allow for control of the graft size prior to implantation and upon implanting into the defect site.

SUMMARY

Methods of soft tissue repair, such as ACL and PCL, are provided. A ligament graft is arranged in a tensioning device and placed adjacent to a heating surface. The ligament graft has a starting length and a starting temperature below body temperature. The ligament graft is simultaneously heated to a temperature that approximates body temperature and tensioned to relax and lengthen the ligament graft to an implanting length. The respective ACL or PCL ligament graft can be implanted into a prepared bone tunnel. The final implanting length is maintained after implantation of the ligament graft into the bone tunnel.

A method of preparing a graft ligament is provided. An allograft having a temperature of less than about 15° C. is placed on a graft preparation substrate. A region of the allograft is placed in a tensioning element on the graft preparation substrate. A water-activated heating element is arranged adjacent to the allograft. A barrier layer is disposed between the water-activated heating element and the frozen allograft. The water-activated heating element and the barrier layer are placed about the allograft such that the barrier layer is adjacent to the allograft. The tensioning element is engaged and the water-activated heating pack is activated to simultaneously heat and tension the allograft.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
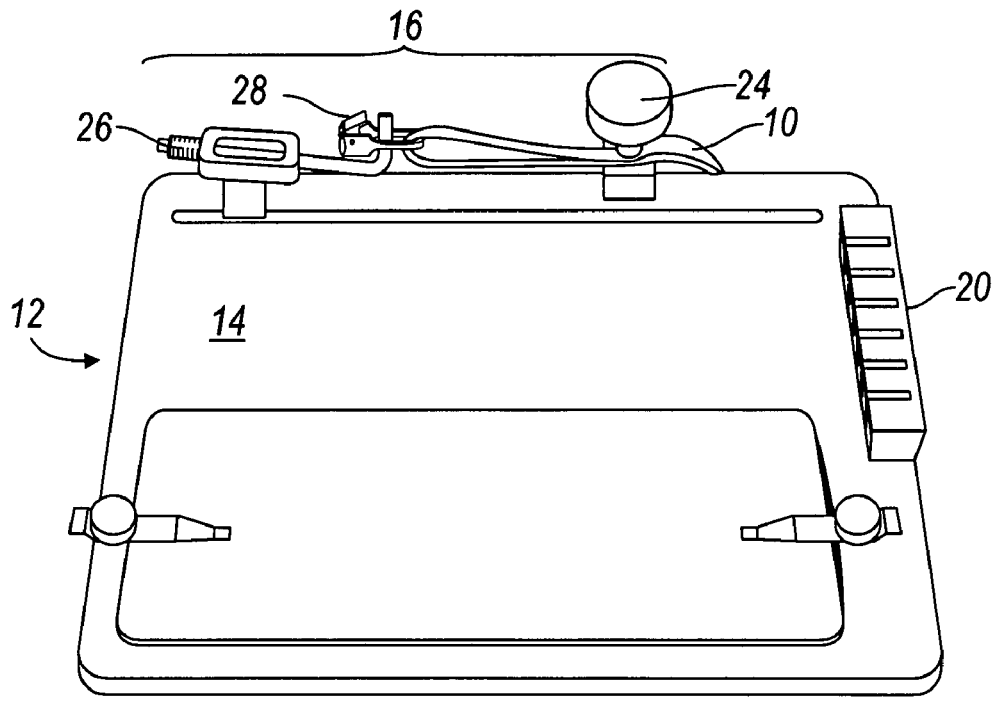
FIG. 1 depicts a graft preparation table having a ligament graft thereon according to the present teachings.
Figure 2:
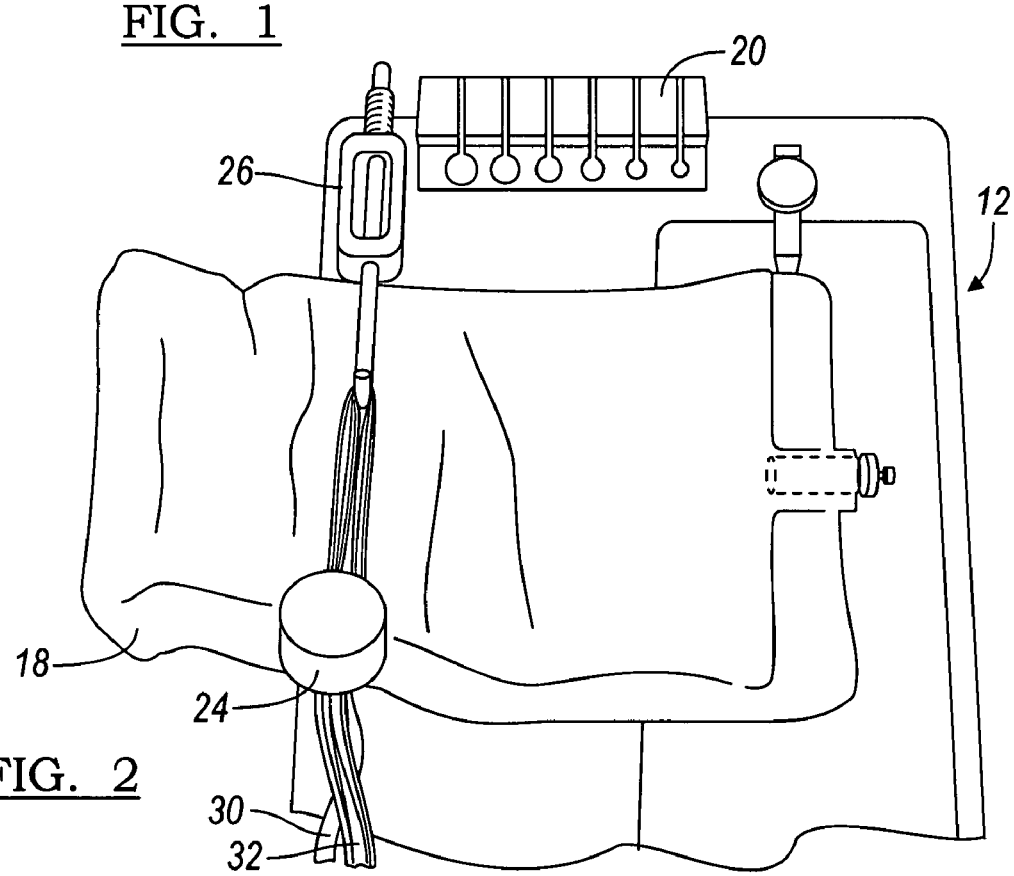
FIG. 2 depicts a heating element disposed under the ligament graft according to the present teachings.

The following description is merely exemplary in nature and is not intended to limit the present disclosure, application, or uses. Although certain examples and surgical methods disclosed herein are in conjunction with the anterior or posterior cruciate ligaments, it is understood that the graft preparation apparatus can be used to prepare any graft for implantation into any area of a patient.

At the outset, an exemplary procedure for preparing a tibial tunnel and a femoral tunnel will be described. For a knee reconstruction involving an unrepairable or torn ACL, the procedure may begin with a general anesthesia being administered to the patient. The patient may be positioned supine on an operating table. A well-padded tourniquet may be placed proximal on the thigh of the affected leg. An arthroscopic leg holder may be placed around the tourniquet. The table may be inclined (e.g. 15 degrees of trendelenburg) and adjusted in height (e.g. waist level) according to the desires of the surgeon. The other leg may be secured to the foot of the table. A Mayo stand may be placed over the leg holder and positioned to permit access to the lateral thigh.

The surgical site may be prepped and draped with a sterile seal. Standard arthroscopic draping may be performed covering the Mayo stand. A light cord, camera, motorized instruments, inflow, outflow, and suction tubing may be wrapped and secured to the drape on the Mayo stand. An irrigation stand may be set up and positioned. The joint of the affected leg may be examined physically to confirm a rupture of the ACL and to determine the amount and degree of movement.

The graft harvesting step in the procedure depends on the type of ACL substitute that is to be utilized. In one example, the gracilis and semi-tendinosus tendons are harvested from the patient and used as the ACL substitute. In general these may provide grafts that are stronger in the joint than the original ACL and have less postoperative morbidity. In other examples, patellar tendons, autogenous tendons, frozen and lyophilized tendon allografts, or some of the various known synthetic materials may be used as the ACL substitute.

After the grafts are obtained, they may be prepared and sized. In one example, a surgical assistant may prepare and size the grafts while the surgeon continues with the rest of the ACL replacement procedure. Sutures may be attached to the ends of the grafts to aid in grasping, manipulating and securing the grafts in place. Incremental sizing tubes may be used to size the grafts and select the appropriate drills for forming the tunnels. The prepared knee may now be examined by arthroscopic procedures. Standard anterolateral and anteromedial portals may be made for the diagnostic arthroscopy. In one example, the lateral portal may be made at a location one-third the width of the patella ligament medial to the lateral margin and positioned vertically just inferior to the inferior patella tip. The medial portal may be made vertically, just inferior to the inferior patella tip and adjacent to the medial border of the patella ligament. The two portals may be located at the same level.

In one example, wallplasty may be performed to remove a portion of the lateral condylar wall. A tool such as an up-angled, curved and uterine curette may be used to remove the origin (and stump) of the ACL from the intercondylar roof and the wall of the lateral femoral condyle. The retained synovial and cruciate remnants may be cleaned and vacuumed with a full-radius resector.

Next, a tibial tunnel is prepared. In one example, a Howell™ 65° Tibial Guide (Howell Guide, not shown) may be used to prepare the tibial tunnel. The Howell Guide and a method of using may be found in U.S. Pat. No. 6,254,605, which is incorporated by reference. Similarly, a Fanelli™ Tibial Guide (Fanelli Guide, not shown) may be used to prepare the tibial tunnel.

Once the tibial tunnel has been prepared, a femoral aimer (not depicted) may be inserted through the tibial tunnel. The femur may then be flexed to 90° relative to the tibia. The femoral aimer may then be laterally angulated and externally rotated away from the PCL (not shown). A graft passing pin may then be drilled through the lateral thigh. A reamer is used to drill the femoral tunnel.

One exemplary method of securing the replacement grafts to the respective bone tunnels includes using interference screws such as a TunneLoc® Interference Screw manufactured by the assignee of the present disclosure. Although the following discussion will be directed toward utilizing interference screws, other methods may be used to secure the respective ligament grafts 10 within the bone tunnel. In embodiments using interference screws, a tunnel notcher (not shown) may be used to notch the anterior rim of the tunnels to facilitate improved contact with the interference screw.

The present teachings provide methods of repairing an ACL or PCL using a ligament graft. The methods advantageously allow for delivery of the ligament graft 10 to the defect site in an appropriately lax state such that the ligament graft 10 maintains substantially the same size (less than about 5% to 10% difference in length or in diameter) from when the graft is in its final relaxed state or implanting length to the in vivo conditions. The ligament graft 10 is simultaneously heated to a temperature that approximates body temperature and tensioned to relax and lengthen the ligament graft 10 from a first starting length to the longer, second implanting length. The ligament graft 10 is implanted into a prepared bone tunnel. The final implanting length is maintained after implantation of the ligament graft 10 into the bone tunnel.

Referring to FIGS. 1 through 4, a ligament graft 10 is arranged on a graft preparation table 12. The ligament graft 10 can include any fresh or frozen autograft or allograft suitable for use as a replacement for the ACL or the PCL. In various embodiments, the ligament graft 10 has a starting temperature which is less than body temperature (about 37° C.). For example, in embodiments where the ligament graft 10 is provided as a frozen allograft, the starting temperature of the ligament graft 10 can be less than about 15° C. To maintain the integrity of the ligament graft 10, the ligament graft 10 should be at least partially thawed prior to use. A partial thawing will allow the ligament graft 10 to stretch without tearing or snapping the tissue.

The graft preparation table 12 includes a working surface 14 and a tensioning element 16. The working surface 14 provides a space for the heating element 18 and any optional guides or tools, such as the sizing guide 20.

The heating element 18 provides a heating surface for increasing the temperature of the ligament graft 10. In various embodiments, the heating surface can be a substantially dry heating surface. As used herein, "substantially dry" refers to an exterior moisture content on the heating element 18 of less than about 5% by weight of the ligament graft 10. The substantially dry surface provides the minimum amount of moisture needed to maintain the integrity of the ligament graft 10 throughout the method without saturating or soaking the ligament graft 10.

The heating element 18 should include a biocompatible surface and the heating element 18 should be easily portable for use in the operating room or at the surgical site. The heating element 18 includes a readily activatable material such as a water-activated heat pack, an air-activated heat pack, and combinations thereof. The heating element 18 can be disposable and pre-sterilized or a multi-use device. The heating element 18 and the readily activatable material should provide heat to the surface of the heating element 18 of less than about 50° C. or from about 40° C. to about 44° C. The heating element 18 transfers heat generated to the ligament graft 10 to heat the ligament graft to approximate a patient's body temperature.

The heating element 18 is disposed about the ligament graft 10. As depicted, the heating element 18 is folded over the ligament graft 10. It is understood that the heating element 18 can be placed on top of the ligament graft 10 without being completely folded over the ligament graft 10, underneath the ligament graft 10 without being completely folded over the ligament graft 10, or underneath the graft preparation table 12 to warm the graft preparation table 12 to indirectly distribute heat to the ligament graft 10. Any other position is suitable in which the heating element 18 is adjacent to the ligament graft 10. The heating element 18 can also be directly connected to the tensioning element 16 such that heat is distributed from the tensioning element 16 to the ligament graft 10.

The heating element 18 can include a moisture-controlled oven. The moisture-controlled oven would maintain a humidity level in the oven to prevent the ligament graft 10 from drying. The tensioning device 16 is engaged while the moisture-controlled oven generates heat.

Figure 3:
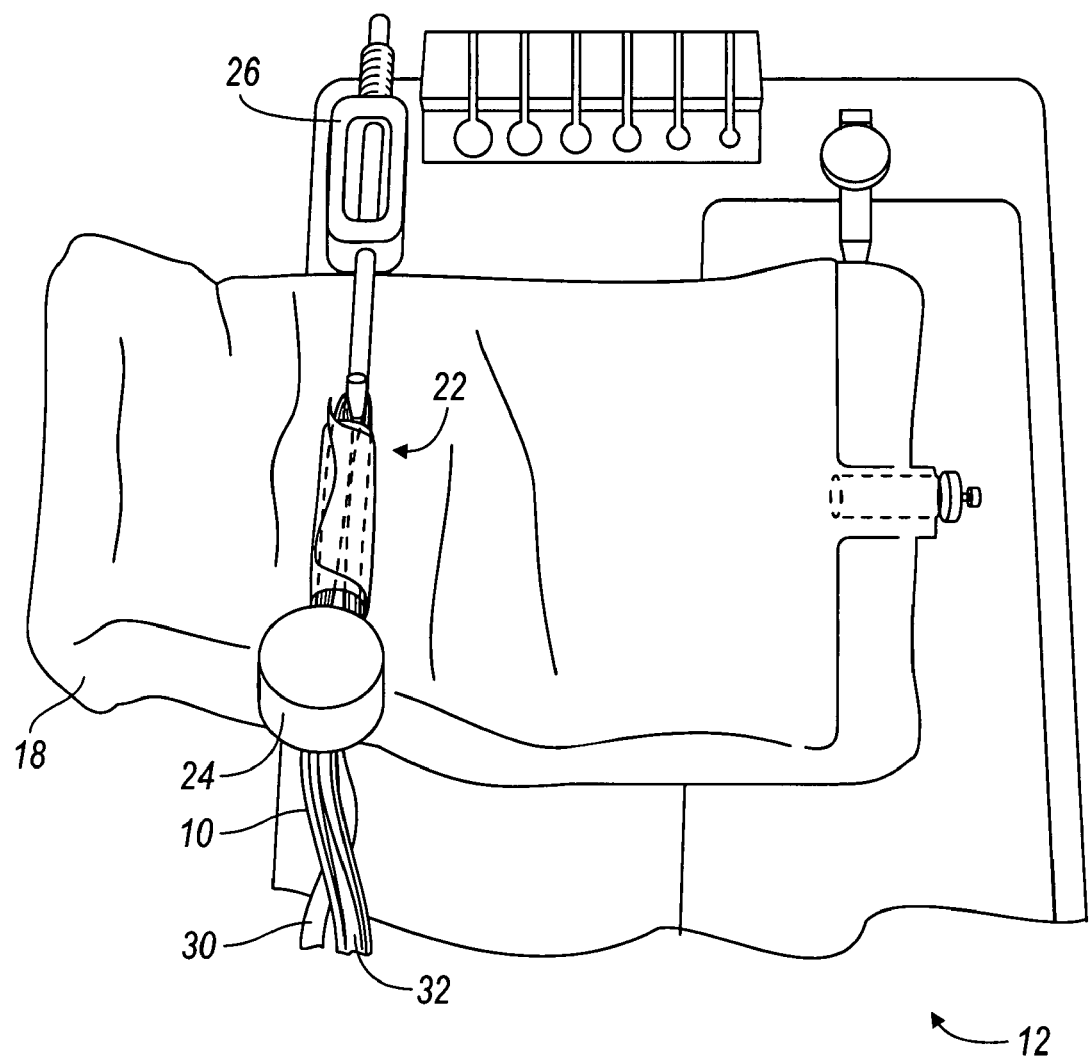
FIG. 3 depicts a barrier layer disposed between the ligament graft and the heating element according to the present teachings.

Heat from the heating element 18 should be controlled to prevent heating the graft to approximate the patient's body temperature and not more than about 40° C. The heat distribution can be modulated using a low-moisture barrier layer 22. The barrier layer 22 can be larger, smaller, or the same size as either of the ligament graft 10 or the heating element 18. As depicted in FIG. 3, the barrier layer 22 is sized to sufficiently envelop a region of the ligament graft 10. The barrier layer 22 is generally a material which can distribute and modulate heat from the heating element 18. The barrier layer 22 can be a flexible material which can be easily sized as needed in the operating room, such as a piece of gauze.

In various embodiments the barrier layer 22 can be dampened to retain the moisture level in the ligament graft 10 during the process. The dampened barrier layer 22 has a moisture content of less than about 10% of the fluid by the weight of the barrier layer 22. Exemplary fluids useful to dampen the barrier layer 22 include aqueous solutions such as sterile water, saline, a buffer solution, or mixtures containing extracorporeal fluids such as blood. To prepare the low-moisture barrier layer 22, a piece of gauze can be dipped into the fluid and the excess fluid can be wrung from the gauze, or the gauze can be misted with the fluid until the desired amount of dampening is achieved.

Tensioning the ligament graft 10 relaxes the fibers such that the ligament graft 10 can be integrated into the implant site and provides the proper range of motion to the knee. The ligament graft 10 can be placed on a tensioning device 16. The tensioning device includes a moveable region 24 and a stationary region 26.

The moveable region 24 is adjusted to apply a force of from about 10 Newtons to about 40 Newtons on the ligament graft 10. Calibration markings can be included on the tensioning device 16 to translate the movement of the moveable region 24 into force applied to the ligament graft 10. The tension applied depends on various factors such as the ligament graft 10 size and the amount of graft relaxation desired. The tension is generally applied to prevent additional lengthening of the ligament graft 10 when the graft is exposed to in vivo conditions. The tensioning device 16 can include any suitable apparatus used to apply a tension within the desired range and to achieve the desired laxity. An exemplary tensioning device 16 includes a spring-loaded system where a spring is engaged to place tension on the ligament graft 10.

The heating and the tensioning of the ligament graft 10 are performed simultaneously. The ligament graft 10 can be heated and tensioned for a period of about 10 minutes, from a period of from about 2 minutes to about 20 minutes, or for a period of more than 20 minutes. This short time period allows for intraoperative preparation of the ligament graft 10 and eliminates the need for preparation of the ligament graft 10 prior to the operation which may lead to multiple changes in graft size, ultimately impacting the range of motion at the implant site and the success of the graft.

As shown in FIGS. 1, 4, and 5A through 5D, an optional securing device 28 can be applied to the ligament graft 10. The securing device 28 can be applied to a loop in the ligament graft (FIG. 1) or the securing device can be applied to the ends 30 and 32 of the ligament graft 10 (FIGS. 4 and 5A through 5D). As shown in FIG. 1, the securing device 28 is attached to the tensioning element 16 and can secure the ligament graft 10 to the bone tunnel using an extendable arm, such as the EZ-Loc® device manufactured by Arthrotek, Inc. of Warsaw, Ind., USA. In such embodiments, the region of the ligament graft 10 which is attached to the securing device 28 is fixed in the femoral tunnel with the securing device 28 and the opposite end of the ligament graft 10 is fixed in the tibial tunnel with any another suitable graft fixation device. An exemplary graft fixation device is a spiked washer, such as those disclosed in U.S. Pat. No. 5,931,869 to Boucher et al, issued Aug. 3, 1999; U.S. Pat. No. 6,280,472 to Boucher et al., issued Aug. 28, 2001; U.S. Pat. No. 6,482,232 to Boucher et al., issued Nov. 19, 2002; and U.S. Pat. No. 6,755,840 to Boucher et al., issued Jun. 29, 2004, all of which are incorporated herein by reference.

Figure 4:
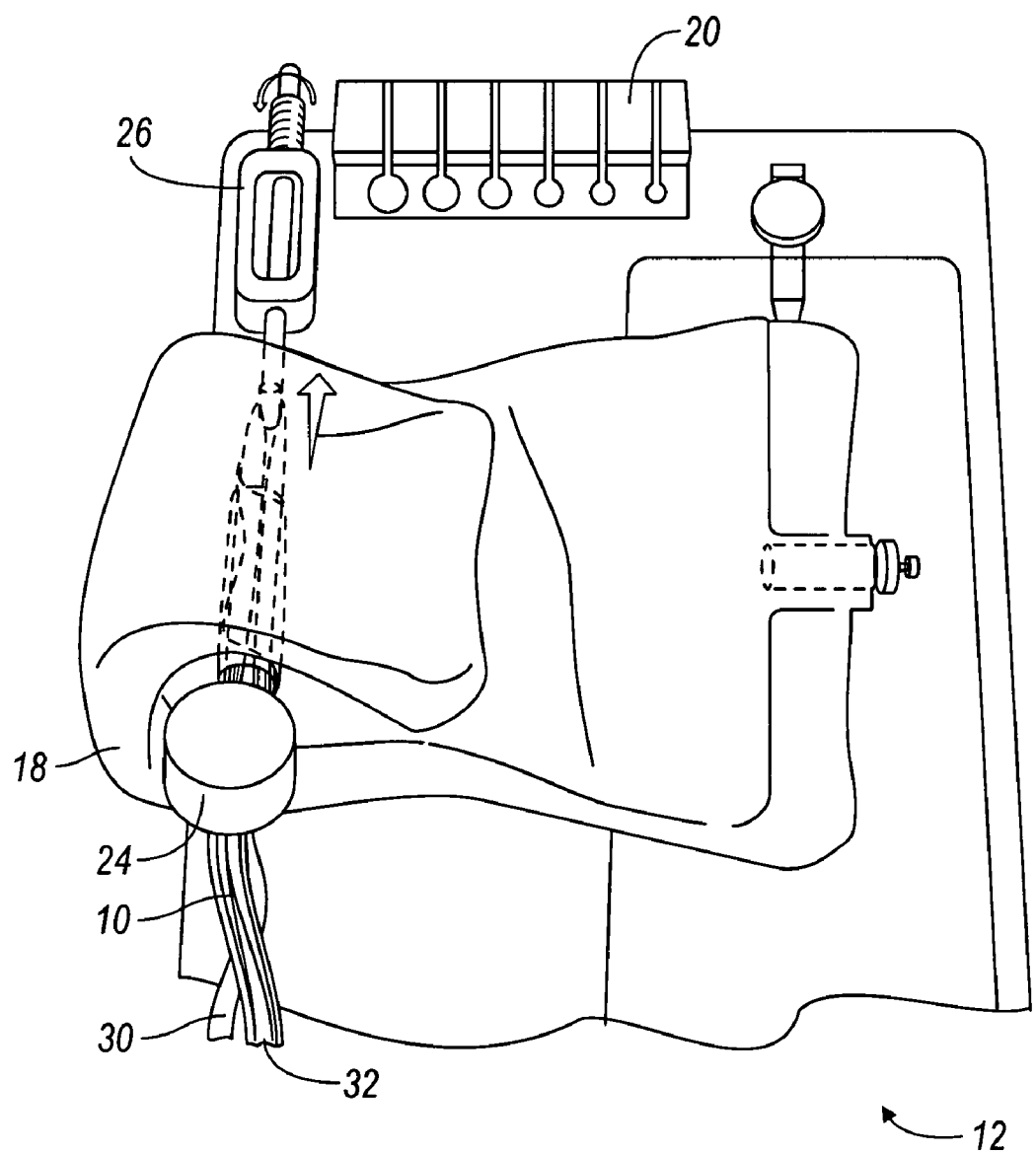
FIG. 4 depicts simultaneously heating and tensioning the ligament graft according to the present teachings.
Figure 5A:
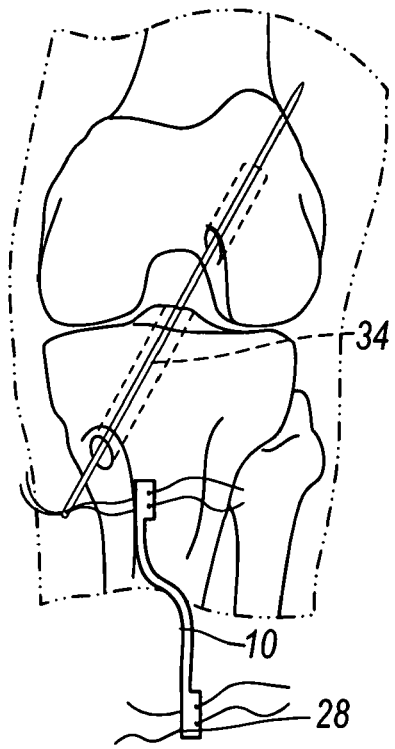
FIGS. 5A through 5D depict an exemplary anterior cruciate ligament repair according to the present teachings.
Figure 5B:
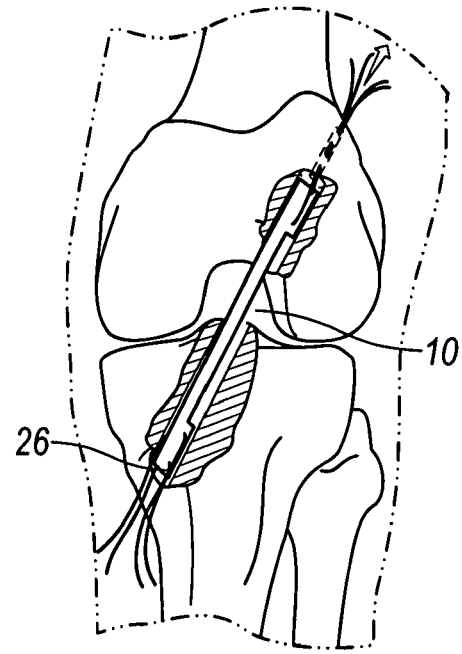
Figure 5C:
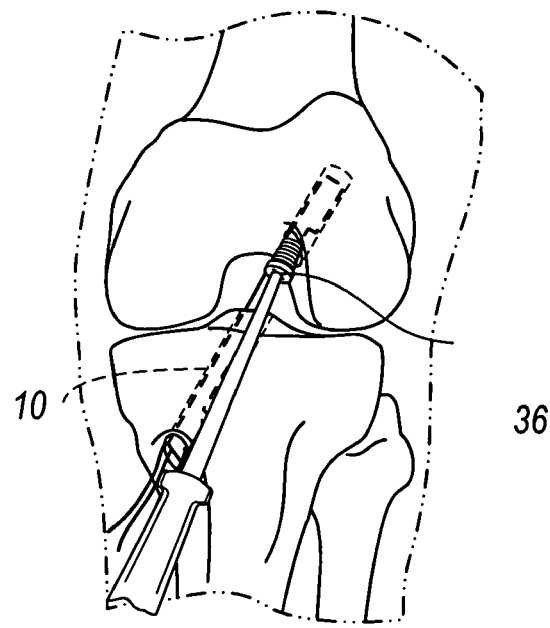
Figure 5D:
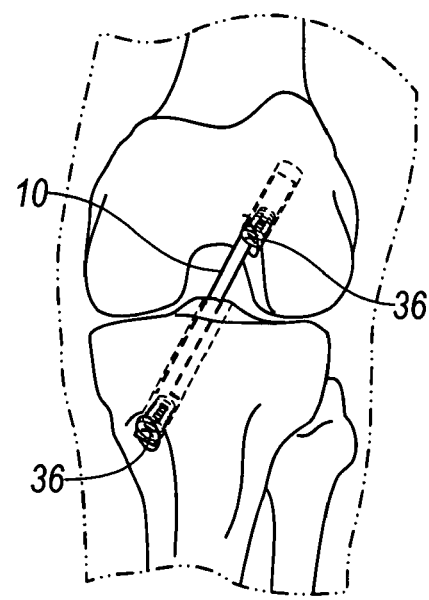

An exemplary embodiment where the securing device 28 is attached to the ends 30 and 32 of the ligament graft 10 is a bone-tendon-bone (BTB) graft as depicted in FIGS. 4 and 5A through 5D. The securing devices 28 on the ends 30 and 32 of the BTB graft are naturally integral with the ligament graft 10. In other embodiments, the ligament graft ends 30 and 32 can be connected to a natural or synthetic securing device 28 using stitches or any suitable mechanical or chemical attachment. As shown in FIG. 4, the ends 30 and 32 of the ligament graft 10 can be accessible during the heating and tensioning of the graft. This allows for the securing device 28 to be attached to the ligament graft 10 while the graft is being relaxed and thereby provides a more efficient surgery.

In various embodiments the graft is minimally shaped prior to heating and stretching. The shaping can include trimming the ligament graft 10 to a more appropriate length or can include resecting regions of the ligament graft 10 to have an appropriate diameter to fit in the bone tunnel. The shape of the ligament graft 10 can be determined using measurements made while preparing the area for the ligament graft 10.

In the ACL or PCL repair, a bone tunnel 34 is prepared. The bone tunnel 34 is sized using the appropriate tools as described above herein. After the ligament graft 10 is heated and tensioned, the ligament graft 10 is advanced through the bone tunnel 34. As depicted, the ligament graft 10 includes bone-securing device 28. The ligament graft 10 can be secured in the tunnel using interference screws 36.

The implanted ligament graft 10 maintains the implanting length after being secured to the bone tunnel 34. The simultaneous heating and tensioning of the ligament graft 10, the quick preparation, and the ease of use of the method in the operating room provide an in situ graft preparation which minimizes additional and unwanted relaxation of the ligament graft 10 and provides the appropriate amount of flexion to the knee.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A method of intraoperative ligament repair comprising:
   a. arranging a ligament graft in a tensioning device located adjacent to a heating element, where the ligament graft has a starting length and a starting temperature below body temperature;
   b. simultaneously heating the ligament graft to a temperature that approximates body temperature and longitudinally tensioning the ligament graft to relax and lengthen the ligament graft to an implanting length during an operative procedure on a patient; and then
   c. implanting the graft into the patient.

2. The method of claim 1, further comprising implanting the ligament graft into a prepared bone tunnel to repair a ligament; wherein the implanting length is substantially maintained after implantation of the ligament graft into the bone tunnel.

3. The method of claim 1, wherein the ligament graft repairs an anterior cruciate ligament.

4. The method of claim 1, wherein the ligament graft repairs a posterior cruciate ligament.

5. The method of claim 1, wherein the implanting length is longer than the starting length.

6. The method of claim 1, wherein the ligament graft starting temperature is less than about 15° C.

7. The method of claim 1, wherein tensioning the ligament graft comprises applying a force of from about 10 Newtons to about 40 Newtons on the ligament graft.

8. The method of claim 1, wherein tensioning the ligament graft comprises applying a sufficient force to prevent additional lengthening of the ligament graft when the graft is exposed to in vivo conditions.

9. The method of claim 1, further comprising activating a heating surface using an activating technique selected from the group consisting of: activating a water-activated heat pack, activating an air-activated heat pack, and combinations thereof.

10. The method of claim 9, wherein the activating technique provides a substantially dry heating surface.

11. The method of claim 9, wherein activating the heating surface generates a heating temperature of less than about 50° C.

12. The method of claim 9, wherein activating the heating surface heats the graft to a temperature of less than about 40° C.

13. The method of claim 1, wherein the ligament graft is heated and tensioned for about 10 minutes.

14. The method of claim 1, further comprising applying a bone attachment region to the ligament graft.

15. The method of claim 14, wherein the bone attachment region is attached while the ligament graft is being tensioned and heated.

16. The method of claim 15, wherein the bone attachment region is attached to the tensioning device.

17. The method of claim 1, further comprising disposing a barrier layer between a heating surface and the ligament graft.

18. The method of claim 17, further comprising dampening the barrier layer with an aqueous solution.

19. The method of claim 18, wherein dampening the barrier layer provides a moisture level of less than about 10% (by weight of the aqueous solution to weight of the dampened barrier layer) to the barrier layer.

20. The method of claim 1, wherein the length of the ligament graft after being implanted into a defect site has less than a 5% difference compared to the ligament graft as taken immediately after tensioning to provide proper laxity to the ligament graft.

21. A method of intraoperative ligament repair comprising:
a. arranging a ligament graft in a tensioning device located adjacent to a substantially dry heating surface, where the ligament graft has a starting length and a starting temperature below body temperature;
b. simultaneously heating the ligament graft to a temperature approximate to body temperature and longitudinally tensioning the ligament graft to relax and lengthen the ligament graft to a final implanting length during an operative procedure on a patient; and then
c. implanting the graft into the patient.

22. The method of claim 21, further comprising implanting the ligament graft into a prepared bone tunnel to repair a posterior cruciate ligament; wherein the final implanting length is maintained after implantation of the ligament graft.

23. The method of claim 21, further comprising implanting the ligament graft into a prepared bone tunnel to repair an anterior cruciate ligament; wherein the final implanting length is maintained after implantation of the ligament graft.

24. A method of intraoperative ligament repair comprising:
a. placing an allograft having a temperature of less than about 15° C. on a graft preparation substrate;
b. placing a region of the allograft in a tensioning element on the graft preparation substrate;
c. arranging a water-activated heating element having a substantially dry surface adjacent to the allograft;
d. disposing a barrier layer between the water-activated heating element and the allograft;
e. placing the water-activated heating element and the barrier layer about the allograft such that the barrier layer is adjacent to the allograft;
f. engaging the tensioning element and activating the water-activated heating element to simultaneously heat and longitudinally tension the allograft to an implanting length during an intraoperative procedure on a patient; and
g. implanting the allograft into the patient.

25. The method of claim 24, wherein the length of the ligament graft after being implanted into a defect site has less than a 5% difference compared to the ligament graft as taken immediately after tensioning to provide proper laxity to the ligament graft.

26. The method of claim 24, wherein implanting the allograft into the patient is conducted while the allograft is at about body temperature.

\* \* \* \* \*